(12) United States Patent
Zagorchev et al.

(10) Patent No.: US 9,588,204 B2
(45) Date of Patent: Mar. 7, 2017

(54) MAGNETIC RESONANCE SPECTROSCOPIC IMAGING VOLUME OF INTEREST POSITIONING

(71) Applicant: KONINKLIJKE PHILIPS N.V., Eindhoven (NL)

(72) Inventors: Lyubomir Georgiev Zagorchev, Burlington, MA (US); Stewart Young, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 427 days.

(21) Appl. No.: 14/363,510

(22) PCT Filed: Dec. 4, 2012

(86) PCT No.: PCT/IB2012/056938
§ 371 (c)(1),
(2) Date: Jun. 6, 2014

(87) PCT Pub. No.: WO2013/084142
PCT Pub. Date: Jun. 13, 2013

(65) Prior Publication Data
US 2014/0320129 A1 Oct. 30, 2014

Related U.S. Application Data

(60) Provisional application No. 61/568,700, filed on Dec. 9, 2011.

(51) Int. Cl.
*G01V 3/00* (2006.01)
*G01R 33/48* (2006.01)
(Continued)

(52) U.S. Cl.
CPC .......... *G01R 33/4828* (2013.01); *A61B 5/055* (2013.01); *A61B 5/7485* (2013.01);
(Continued)

(58) Field of Classification Search
USPC .......................................................... 324/309
See application file for complete search history.

(56) References Cited

U.S. PATENT DOCUMENTS 6,430,430 B1 * 8/2002 Gosche ................ G06T 7/0012
128/920
2004/0218796 A1 11/2004 Ryner et al.
(Continued)

FOREIGN PATENT DOCUMENTS

JP 2011156108 A 8/2011
WO 2011050348 A2 4/2011

OTHER PUBLICATIONS

Zagorchev, L. et al. "Manual annotation, 3-D shape reconstruction, and traumatic brain injury analysis", Int'l Workshop Multimodal Brain Image Analysis (MBIA), Lecture Notes in Computer Science, vol. 7012, pp. 52-59, Toronto, CA Sep. 2011.
(Continued)

*Primary Examiner* — Rodney Fuller

(57) ABSTRACT

A MRSI system (100) includes a structure of interest identifier (206) that identifies a predetermined segmented structure in segmented MRI image data, a positioning rules bank (210) which stores rules for positioning a volume of interest with respect to the identified predetermined segmented structure of the segmented MRI image data, and a volume of interest generator (208) that positions the volume of interest with respect to the identified predetermined segmented structure based on one or more of the rules for positioning the volume of interest with respect to the identified predetermined segmented structure and generates a signal indicative thereof, wherein the signal is analyzed to determine a biochemical composition of a predetermined region of the structure of interest.

15 Claims, 5 Drawing Sheets

(51) Int. Cl.

| | |
|---|---|
| *A61B 5/055* | (2006.01) |
| *G01R 33/483* | (2006.01) |
| *G01R 33/485* | (2006.01) |
| *G01R 33/56* | (2006.01) |
| *A61B 5/00* | (2006.01) |
| *G01R 33/54* | (2006.01) |

(52) U.S. Cl.
CPC ......... *G01R 33/483* (2013.01); *G01R 33/485* (2013.01); *G01R 33/5608* (2013.01); *G01R 33/543* (2013.01)

(56) References Cited

U.S. PATENT DOCUMENTS

| | | | |
|---|---|---|---|
| 2009/0143669 A1* | 6/2009 | Harms | A61B 5/055 600/410 |
| 2010/0260396 A1 | 10/2010 | Brandt et al. | |
| 2011/0116698 A1 | 5/2011 | Weis et al. | |
| 2011/0235887 A1* | 9/2011 | Bertsch | A61B 5/055 382/132 |
| 2014/0355844 A1* | 12/2014 | Menini | G06T 11/006 382/121 |

OTHER PUBLICATIONS

Zagorchev, L. et al. "Evaluation of Traumatic Brain Injury patients using a shape-constrained deformable model". Int'l Workshop Multimodal Brain Image Analysis (MBIA), pp. 118-125, Toronto, CA Sep. 2011.

Sharma, R. "Molecular Imaging by Proton Magnetic Resonance Imaging (MRI) and MR Spectroscopic Imaging (MRSI) in Neurodegeneration". Informatica Medica Slovenica, vol. 10, No. 1, Jun. 30, 2005, pp. 35-55, p. 36, col. 2—p. 39, figures 1,2,4,5, p. 41, col. 2, paragraph 3, p. 42 col. 1, paragraph 2, p. 53.

Khurd, P. et al. "Facilitating 3D Spectroscopic Imaging through Automatic Prostate Localization in MR Images Using Random Walker Segmentation Initialized via Boosted Classifiers", Sep. 22, 2011, Prostate Cancer Imaging, Image Analysis and Image-Guided Interventions, Springer Berlin, vol. 6963, pp. 47-56, 2011.

Mason, G.F. et al. "Evaluation of 31P metabolite differences in human cerebral gray and white matter" Magnetic Resonance in Medicine, vol. 39, No. 3 Mar. 1, 1998, pp. 346-353.

Weber-Fahr, W. et al. "A fully automated method for tissue segmentation and CSF-Correction of proton MRSI Metabolites Corroborates Abnormal Hippocampal NAA in Schizophrenia", Neuroimage, vol. 16, No. 1, May 1, 2002, pp. 49-60.

Starck, G. et al. "A 1H magnetic resonance spectroscopy study in adults with obsessive compulsive disorder: relationship between metabolite concentrations and symptom severity" Journal of Neural Transmission; Basic Neurosciences, Genetics and Immunology, Parkinson's disease and allied Conditions, Alzheimer's Disease and Adolescent Psychiatry Related Disorders, Biological Psychiatry, Biological Child and Adolescent Psychiat, vol. 115, No. 7, Jun. 5, 2008, pp. 1051=1-62.

Dydak, U. et al. "In Vivo Measurement of Brain GABA Concentrations by Magnetic Resonance Spectrosopy in Smelters Occupationally Exposed to Manganese" Environmental Health Perspectives, vol. 119, No. 2, Sep. 28, 2010, pp. 219-224.

McRobbie, D.W. et al. MRI from picture to proton. 2nd Edition. Cambridge University Press. 2003.

Pitiot, A. et al. "Expert Knowledge guided segmentation system for brain MRI". Lecture Notes in Computer Science, vol. 2879, 2003, pp. 644-652.

Martin, S. et al "Automated Segmentation of the Prostate in 3D MR Images Using a Probabilistic Atlas and a Spatially Constrained Deformable Model". Medical Physics, Apr. 2010:37(4): 1579-90.

* cited by examiner

MAGNETIC RESONANCE SPECTROSCOPIC IMAGING VOLUME OF INTEREST POSITIONING

This application is a national stage application under 35 U.S.C. §371 of International Application No. PCT/IB2012/056938 filed on Dec. 4, 2012 and published in the English language on Jun. 13, 2013 as International Publication No. WO/2013/084142, which claims priority to U.S. Application No. 61/568,700 filed on Dec. 9, 2011, the entire disclosures of which are incorporated herein by reference.

The following generally relates to Magnetic Resonance Spectroscopic Imaging (MRSI) and more particularly to positioning a volume of interest, such as a voxel, in segmented structure in Magnetic Resonance Imaging (MRI) image data, which localizes the volume of interest for Magnetic Resonance Spectroscopic (MRS) biochemical composition analysis.

MRS is a non-invasive analytical technique that can be used to determine biochemical composition in-vivo in association with, for example, neurodegenerative disorders such as brain tumors, strokes, seizure disorders, and Alzheimer's disease. With MRS, the MR signal produces a spectrum of resonances that correspond to different molecular arrangements of an isotope being "excited." This signature has been used to determine information about metabolic disorders affecting the brain and to provide information about tumor metabolism.

MRSI combines MRI and MRS. In this combination, a volume of interest (VOI) is used to spatially localize spectra from which MRS determines the biochemical composition for the VOI. Generally, a single voxel is used to define the VOI, and the accuracy of the position of the voxel affects the outcome of the determination of the biochemical composition. That is, if the voxel is intended to be inside certain structure, then positioning the voxel such that a portion of it is outside the structure will result in a less accurate reading as biochemical composition other than the structure is also captured.

With current state of the art MRSI, the user, in one instance, manually positions the voxel in the structure. Unfortunately, it can be difficult to manually and accurately position a voxel in the structure, especially for small structures. To complicate matters, the voxel is typically constrained, for practical reasons, to be rectangular, whereas structure tends to be irregular in shape. Again, inaccurate positioning can lead to less accurate or even inaccurate results. In some instances, multiple procedures (e.g., corresponding to different contrast images) are performed to facilitate positioning, which makes the process tedious and time consuming.

Furthermore, even with larger structures where it is easier to position a voxel in the structure or in instances in which the volume of interest is not entirely in the structure, being able to manually position a voxel at the same position in image data from different studies (e.g., an initial study and a follow up study) can be difficult. In this instance, results from two studies performed at two different times may not be able to be used to determine whether a disease has regressed, advanced or stayed the same, as the two voxels may not represent the same portion of the structure of interest.

Aspects described herein addresses the above-referenced problems and others.

In one aspect, a MRSI system includes a structure identifier that identifies a predetermined segmented structure in segmented MRI image data, a positioning rules bank which stores rules for positioning a volume of interest with respect to the identified predetermined segmented structure of the segmented MRI image data, and a volume of interest generator that positions the volume of interest with respect to the identified predetermined segmented structure based on one or more of the rules for positioning the volume of interest with respect to the identified predetermined segmented structure and generates a signal indicative thereof, wherein the signal is analyzed to determine a biochemical composition of a predetermined region of the structure of interest.

In another aspect, a method includes identifying predetermined segmented structure in segmented MRI image data, positioning a volume of interest with respect to the identified predetermined segmented structure based on one or more of the rules for positioning the volume of interest with respect to the identified predetermined segmented structure and generating a signal indicative thereof, wherein the signal is analyzed to determine a biochemical composition of a predetermined region of the segmented structure.

In another aspect, a MRSI system includes an MRI scanner configured to scan a subject and generate MRI image data indicative thereof, a volume of interest positioner that determines a portion of the MRI image data to analyze, and a MRS analyzer configured to analyze the portion and determine a biochemical composition of a predetermined region positioned with respect to the structure of interest, wherein the biochemical composition corresponds to neurodegenerative disorder. The volume of interest positioner includes a structure identifier that identifies a predetermined segmented structure in the MRI image data, a positioning rules bank which stores rules for positioning a volume of interest with respect to the identified predetermined segmented structure of the MRI image data, and a volume of interest generator that positions the volume of interest with respect to the identified predetermined segmented structure based on one or more of the rules for positioning the volume of interest with respect to the identified predetermined segmented structure and generates a signal indicative thereof.

The invention may take form in various components and arrangements of components, and in various steps and arrangements of steps. The drawings are only for purposes of illustrating the preferred embodiments and are not to be construed as limiting the invention.

FIG. 1 schematically illustrates an example MRSI system which includes a volume of interest positioner.

FIG. 2 schematically illustrates an example of the volume of interest positioner.

Figure 2:
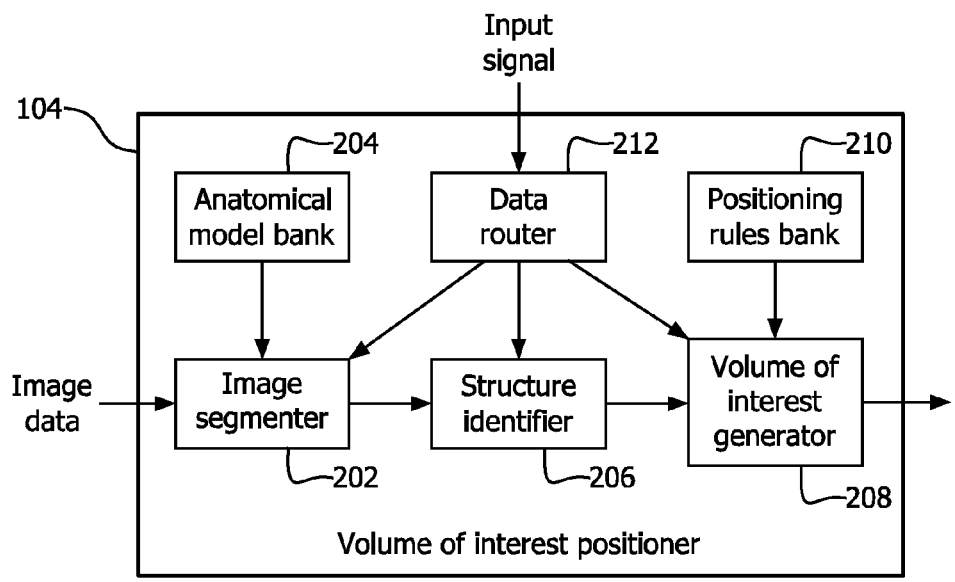
Figure 6:
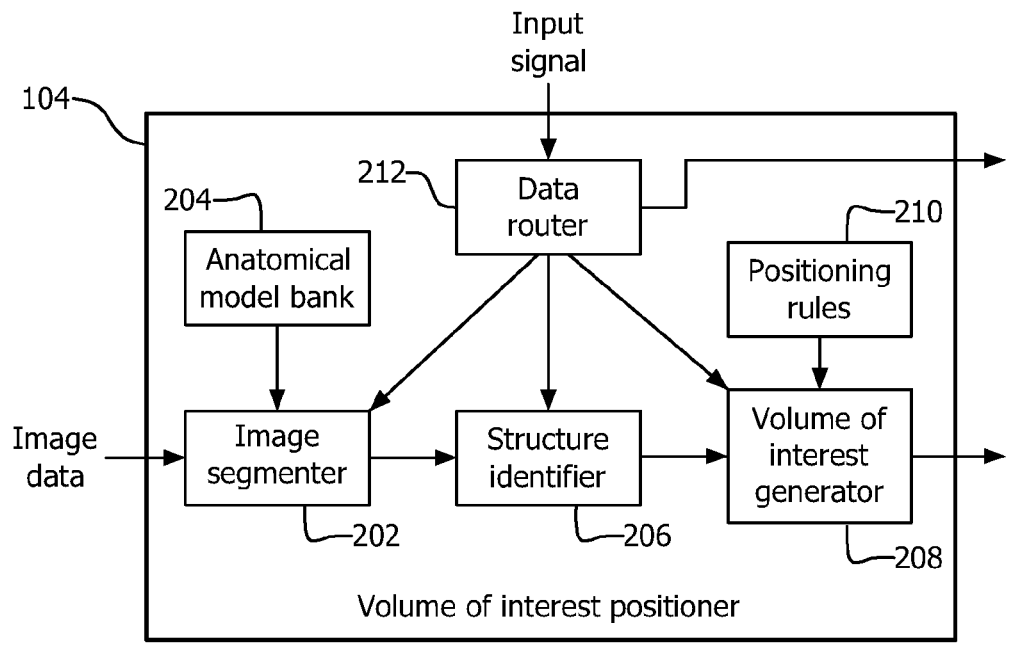

FIG. 6 schematically illustrates a variation of FIG. 2 in which the indicia indicating the segmented structure is also output.

Figure 7:
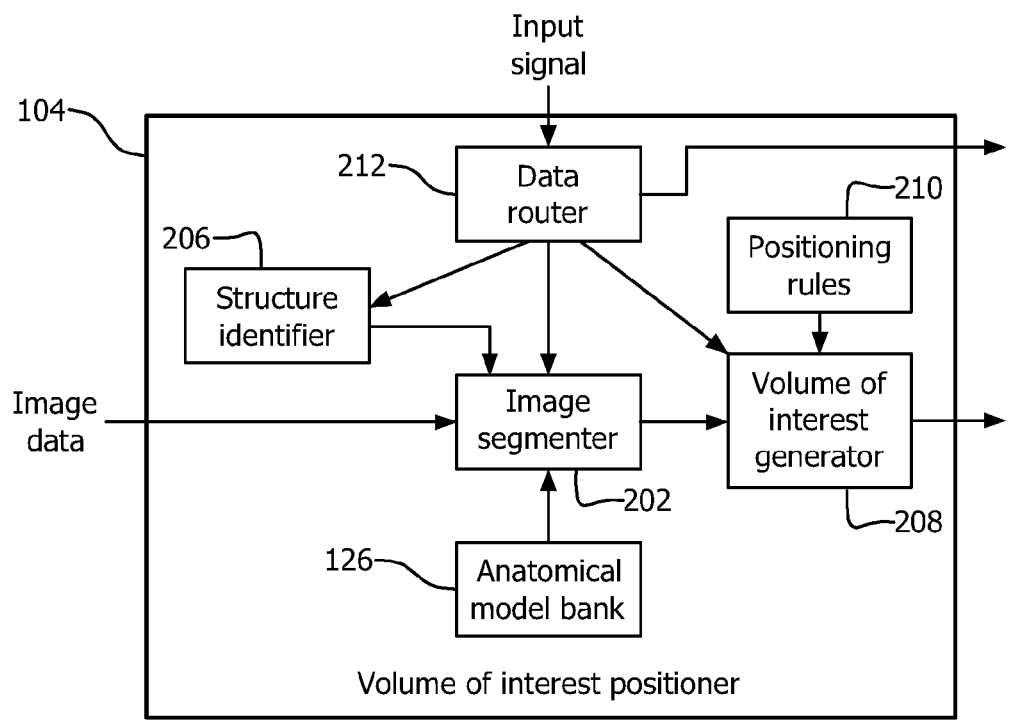

FIG. 7 schematically illustrates a variation of FIG. 2 in which the segmented structure is identified prior to image segmentation.

Figure 8:
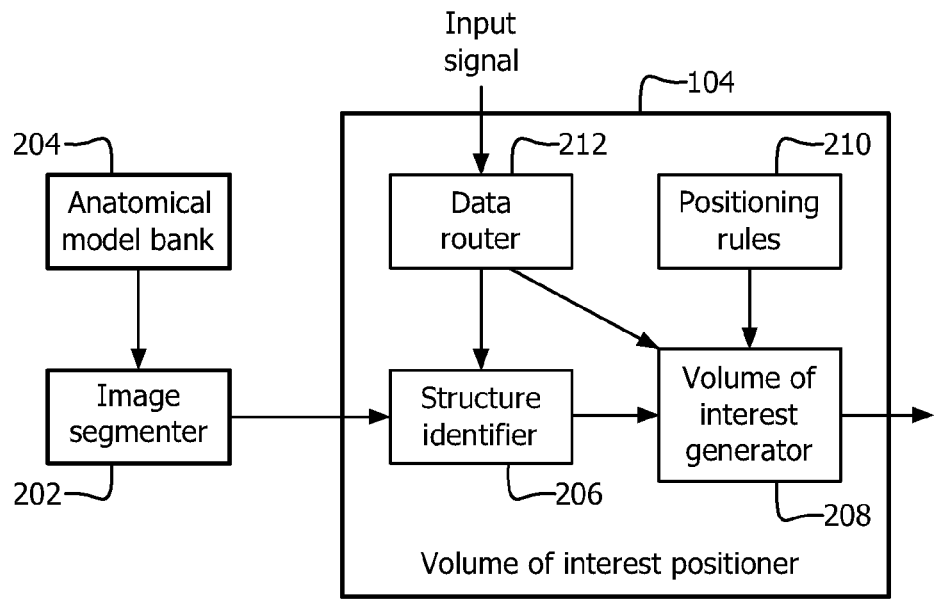

FIG. 8 schematically illustrates a variation of FIG. 2 in which the image segmenter and the anatomical model bank are not part of the volume of interest positioner.

Figure 9:
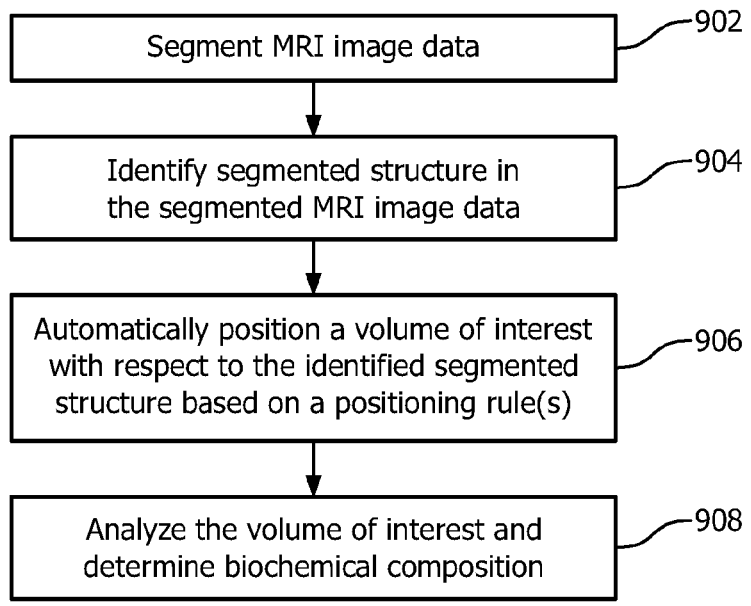

FIG. 9 illustrates a method for positioning a volume of interest with respect to structure segmented in MRI image data.

Figure 1:
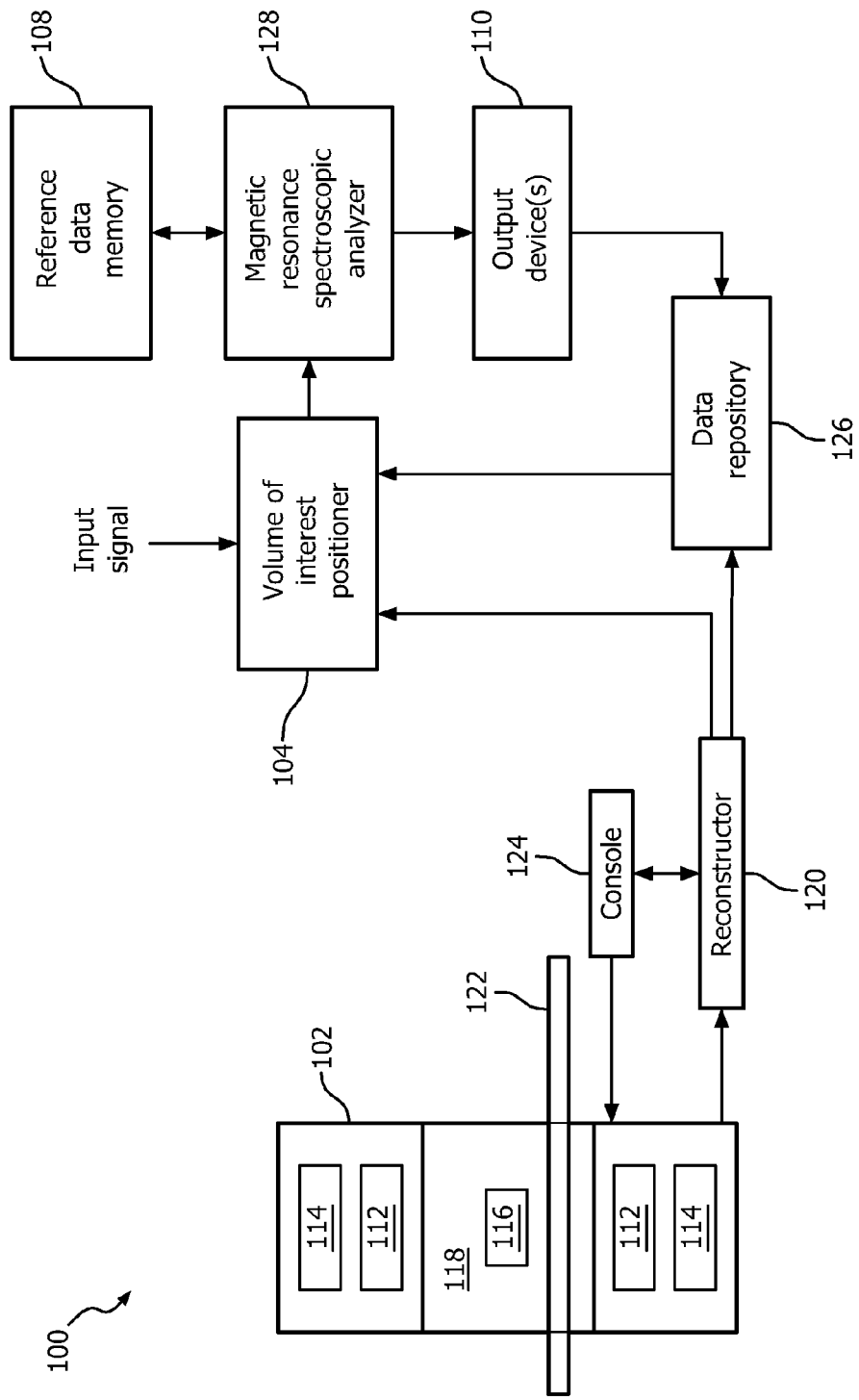

Initially referring to FIG. 1, MRSI system 100 is schematically illustrated. The system 100 includes an MRI scanner 102, a volume of interest positioner 104 and an MRS analyzer 128, which is shown in communication with reference data memory 108 and one or more output devices (output device(s)) 110.

The MRI scanner 102 includes a main magnet 112, gradient (x, y and/or z) coils 114, and an RF coil 116. The main magnet 112 (which can be a superconducting, resistive, permanent, or other type of magnet) produces a substantially homogeneous, temporally constant main magnetic field $B_0$ in an examination region 118. The gradient coils 114 generate time varying gradient magnetic fields along the x, y and/or z-axes of the examination region 118.

The illustrated RF coil 116 includes a transmission portion that transmits a radio frequency signal (e.g., at the Larmor frequency of nuclei of interest such as hydrogen, Helium, etc.) that excites the nuclei of interest in the examination region 118 and a receive portion that receives MR signals emitted by excited nuclei. The transmission and receive portions can alternatively be located in separate coils. An MR reconstructor 120 reconstructs the MR signals and generates MRI image data.

A subject support 122 supports a subject such as a human or animal patient in the examination region 116. A general purpose computing system serves as an operator console 124 and includes an output device such as a display and an input device such as a keyboard, mouse, and/or the like. Software resident on the console 124 allows the operator to interact with the scanner 102, for example, to select an imaging protocol, to initiate scanner, etc.

A data repository 126 can be used to store the image data generated by the scanner 102 and/or other image data. The illustrated data repository 126 may include one or more of a picture archiving and communication system (PACS), a radiology information system (RIS), a hospital information system (HIS), an electronic medical record (EMR) database, a sever, a computer, and/or other data repository. The data repository 126 can be local to the system 100 or remote from the system 100.

The volume of interest positioner 104 is configured to automatically position a volume of interest, such as one or more voxels, with respect to structure segmented in MRI image data obtained from the scanner 102, the repository 126 and/or other source. The illustrated volume of interest positioner 104 receives an input signal, which can include indicia indicating an anatomical model of interest, particular segmented structure, a positioning rule of interest, and/or other information. As described in greater detail below, in one instance the volume of interest positioner 104 utilizes this input to accurately and reproducibly position a volume of interest with respect to segmented in the MRI image data for MRS analysis. In one instance, this may allow for fully-automatic and accurate volume of interest positioning, which may simplify MRSI planning and/or decrease overall time relative to manual positioning approaches. It is to be appreciated that the functions of the volume of interest positioner 104 can be implemented via a processor executing one or more computer readable instructions encoded or embedded on computer readable storage medium such as physical memory. Additionally or alternatively, at least one of the one or more computer readable instructions executed by the processor is carried by a carrier wave, a signal, or other non-computer readable storage medium such as a transitory medium.

The MRS analyzer 128 analyzes the volume of interest. This includes quantifying biochemical composition in the volume of interest with respect to the segmented structure and/or comparing the quantified value and/or a change in the quantified value over time with a predetermined threshold to determine whether a disease has regressed or progressed. The accurate positioning of the volume of interest also allows for accurate and reproducible quantification of biochemical composition, development of biochemical biomarkers from MRI image data for certain diseases as the biochemical composition for a disease will generally be the same across patients, development of a database of reference data based on MRI image data for known "normal" patients and known "diseased" patients, and/or extraction/query of information from a segmentation using the normative dataset. It is to be appreciated that the functions of the MRS analyzer 128 can be implemented via a processor executing one or more computer readable instructions encoded or embedded on computer readable storage medium such as physical memory. Additionally or alternatively, at least one of the one or more computer readable instructions executed by the processor is carried by a carrier wave, a signal, or other non-computer readable storage medium such as a transitory medium.

The reference data memory 108 can be used to store results of MRS analysis, including the quantified biochemical composition information, the change in quantified biochemical composition information, the results of the comparison of the quantified biochemical composition information, the results of the comparison of the change in quantified biochemical composition information, the biochemical biomarkers, the database of normative and abnormal reference data, and/or other information. The output device 110 can be used to visually display, transfer and/or otherwise disseminate the information. The output device 110 may include a display monitor, portable memory, a printer, and/or other output device.

FIG. 2 schematically illustrates an example of the volume of interest positioner 104.

Figure 3:
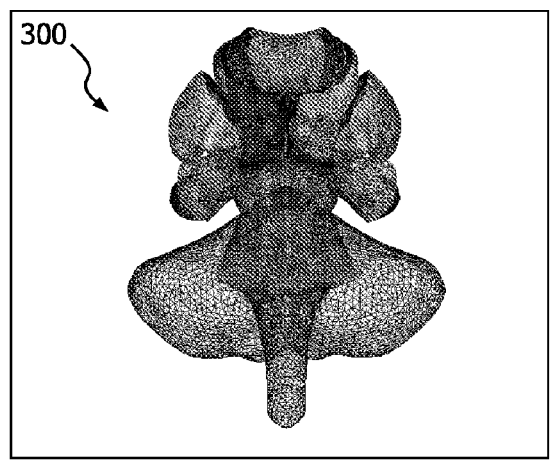
FIG. 3 illustrates an example anatomical model.

An image segmenter 202 receives the MRI image data and obtains an anatomical model of interest from an anatomical model bank 204. An example anatomical model of interest 300 is shown in FIG. 3. The illustrated model of interest 300 represents a human brain. However, it is to be understood that the model of interest 300 may represent other anatomy. In addition, there may be more than one brain model, for example, one for infants, one for pediatrics and one for adults. The illustrated model of interest 300 is a surface representation of a shape-constrained deformable brain model.

Examples of suitable brain models are described in L. Zagorchev, A. Goshtasby, K. Paulsen, T. McAllister, S. Young, and J. Weese, Manual annotation, 3-D shape reconstruction, and traumatic brain injury analysis, Int'l Workshop Multimodal Brain Image Analysis (MBIA), Toronto, Calif., September 2011, and L. Zagorchev, C. Meyer, T. Stehle, R. Kneser, S. Young, and J. Weese, Evaluation of Traumatic Brain Injury patients using a shape-constrained deformable model, Int'l Workshop Multimodal Brain Image Analysis (MBIA), Toronto, Calif., September 2011. Other models are also contemplated herein.

The image segmenter 202 is configured to segment the anatomy represented in the MRI image data based on the anatomy represented in the model of interest 300. In one non-limiting instance, this includes performing an initial registration between the model of interest 300 and the MRI image data, transforming the model of interest 300 to the anatomy in the MRI image data based on a transform (e.g., the Hough transform), performing a parametric adaptation of the model of interest 300 (e.g., pose and/or piecewise), and performing a deformable adaptation of the model 300. Other known techniques can alternatively be used.

A structure identifier 206 identifies one or more segmented structures of the segmented MRI image data. For example, where the input signal includes information identifying the hippocampus, the structure identifier 206 identifies the segmented hippocampus in the segmented MRI image data.

A volume of interest generator 208 generates a volume of interest to be positioned with respect to the identified segmented structure. In the illustrated example, the volume of interest generator 208 generates and positions the volume of interest based on one or more positioning rules of a positioning rules bank 210. The particular positioning rule may be determined based on the information in the input signal and/or otherwise.

Figure 4:
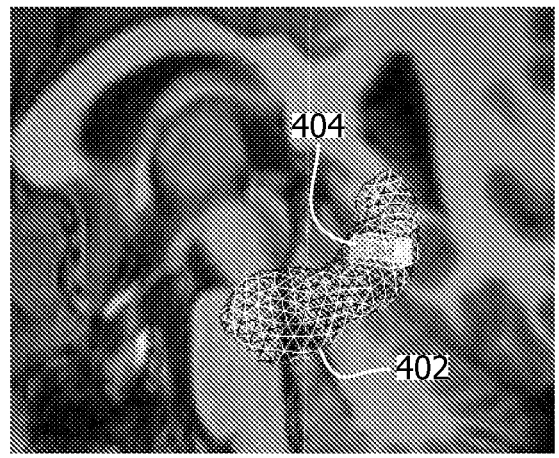
FIG. 4 illustrates an example of a rectangular volume of interest positioned inside a structure segmented in MRI image data.

One rule may indicate that a rectangular voxel volume of interest be placed completely inside the outer surface boundary of the identified segmented structure. FIG. 4 shows the placement of a rectangular voxel 402 completely inside an irregular shaped segmented structure 404. In this example, the segmented structure 404 is represented via a mesh, and the voxel 402 is positioned in the mesh using mesh vertices as anchors. For a rectangular voxel, the vertices include the eight (8) corners, and the volume of interest is placed to satisfy constraints imposed by the locations of the mesh vertices, dependent upon the particular criteria desired by the user, for example, that the voxel is fully contained within the boundaries of the structure of interest.

Returning to FIG. 3, another rule may indicate that a square voxel volume of interest be placed X % inside and (1–X) % outside of the outer surface boundary of the identified segmented structure. Another rule may indicate that a spherical volume of interest be placed completely outside of the surface boundary of the identified segmented structure, but within a predetermined x,y,z coordinate therefrom.

Figure 5:
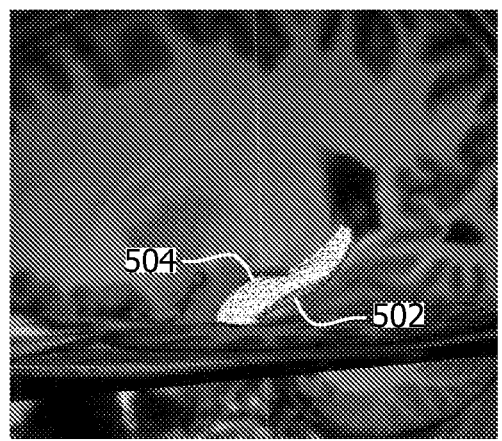
FIG. 5 illustrates an example of an irregular shaped volume of interest positioned inside a structure segmented in MRI image data.

Another rule may indicate that an irregular shape volume of interest be placed inside the surface boundary so as to conform to the entire shape of the identified segmented structure or a subportion thereof. Irregular shaped voxels could be defined by masking the volume within a structure of interest. FIG. 5 shows the placement of an irregular shaped voxel 502 inside an irregular shaped segmented structure 504.

Returning to FIG. 3, another rule may indicate a location within the identified segmented structure to place the volume of interest. For example, a rule may indicate whether the volume of interest is placed at the head, middle and/or tail of the segmented structure (e.g., the hippocampus). Another rule may indicate the positioning of multiple volumes of interest. Other rules are also contemplated herein.

In one instance, the volume of interest generator 208 can be trained to position the volume of interest. In this instance, a user initially manually positions a volume of interest. The volume of interest generator 208 then can automatically position a subsequent same volume of interest based on the manual placement. The volume of interest generator 208 then can automatically positions a next volume of interest based on one or more of the manual placements and previous automatic placement. This can be repeated one or more times. In addition, the user can modify the position of the volume of interest.

A data router 212 routes the information in the input signal. For example, information corresponding to the model of interest is routed to the image segmenter 202, information corresponding to the segmented structure is routed to the structure of interest identifier 206, and information corresponding to the positioning rule of interest is routed to the volume of interest generator 208.

The volume of interest positioner 104 outputs at least a signal indicative of the volume of interest positioned in the segmented structure. As shown in FIG. 1, this signal is provided to the MRS analyzer 128, which can analyze the volume of interest as discussed herein and/or otherwise.

Variations are contemplated.

FIG. 6 shows a variation in which the date router 212 also routes the indicia indicating the segmented structure to the MRS analyzer 128 (FIG. 1). With this indicia, the MRS analyzer 128 can automatically obtain suitable reference data from the reference data memory 130 (FIG. 1) without user interaction. Such reference data can include, for example, biochemical normative data to compare with the biochemical data or change therein determined from the volume of interest.

FIG. 7 shows a variation in which the structure of interest is first identified, and the image segmenter 202 segments a subset of structure such as only the identified structure from the MRI image data. The volume of interest is then placed with respect to the segmented structure as described herein.

FIG. 8 shows a variation in which the image segmenter 202 and the anatomical model bank 204 are separate from and not part of the volume of interest positioner 104.

FIG. 9 illustrates a method for positioning a volume of interest in structure of interest in MRI image data.

It is to be appreciated that the ordering of the acts in the methods described herein is not limiting. As such, other orderings are contemplated herein. In addition, one or more acts may be omitted and/or one or more additional acts may be included.

At 902, MRI image data is segmented, producing segmented MRI image data in which different anatomical structure represented in the MRI image data is segmented. As discussed herein, this may include using a predefined anatomical model.

At 904, a segmented structure is identified in the segmented MRI image data. The identified segmented structure is identified based on input including information indicative of particular structure selected by a user.

At 906, a volume of interest is automatically positioned with respect to the identified segmented MRI image data based on one or more positioning rules. The one or more rules include instructions which allow the volume of interest to be accurately and reproducibly positioned in the same segmented structure in the same and/or different segmented MRI image data.

At 908, the volume of interest is analyzed to determine a biochemical composition of the tissue represented by volume of interest.

The above may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A MRSI system, comprising:
a structure identifier that is configured to identify a predetermined segmented structure in segmented MRI image data;
a positioning rules bank which is configured to store rules for positioning a volume of interest with respect to the identified predetermined segmented structure of the segmented MRI image data for a MRSI data acquisition; and
a volume of interest generator that is configured to position the volume of interest with respect to the identified predetermined segmented structure based on one or more of the rules for positioning the volume of interest with respect to the identified predetermined segmented structure and that is configured to perform the MRSI data acquisition of a signal from the volume of interest,
wherein the MRSI system is configured to analyze the signal from the volume of interest to determine a biochemical composition of a predetermined region of the predetermined segmented structure, wherein the predetermined region of the predetermined segmented structure corresponds to the volume of interest.

2. The MRSI system of claim 1, wherein the predetermined segmented structure is represented as a mesh, and the volume of interest generator is configured to position the volume of interest with respect to the predetermined segmented structure using mesh vertices as anchors.

3. The MRSI system of claim 1, wherein the volume of interest is positioned completely inside of the predetermined segmented structure; or
wherein the volume of interest is positioned partially inside and partially outside of the predetermined segmented structure; or
wherein the volume of interest is positioned completely outside of the predetermined segmented structure.

4. The MRSI system of claim 1, wherein the volume of interest generator is configured to position the volume of interest at a first location with respect to the predetermined segmented structure in first image data and at a second location with respect to the predetermined segmented structure in second image data, wherein the first and second location are substantially the same location.

5. The MRSI system of claim 1, wherein the volume of interest generator is configured to position the volume of interest based at least on one or more previously positioned volumes of interest.

6. The MRSI system of claim 1, wherein the volume of interest includes one or more voxels; and/or
wherein the volume of interest is not cuboidal and not spherical in shape.

7. The MRSI system of claim 1, wherein the biochemical composition is indicative of a neurodegenerative disorder of a patient corresponding to the MRI image data.

8. The MRSI system of claim 1, wherein the volume of interest is one of cuboidal, spherical, or not cuboidal and not spherical in shape.

9. The MRSI system of claim 1, comprising:
an MRI scanner configured to scan a subject and generate MRI image data indicative thereof;
volume of interest positioner, including:
the structure identifier
the positioning rules bank and
the volume of interest generator; and
an MRS analyzer configured to analyze the signal from the volume Of interest and to determine the biochemical composition of the predetermined region of the predetermined segmented structure, wherein the biochemical composition corresponds to neurodegenerative disorder.

10. A method, comprising:
identifying a predetermined segmented structure in segmented MRI image data; and
positioning a volume of interest with respect to the identified predetermined segmented structure for a MRSI data acquisition, wherein the positioning is based on one or more rules for positioning the volume of interest in the identified predetermined segmented structure, wherein the rules for positioning the volume of interest are stored in a positioning rules bank, and
performing the MRSI data acquisition of a signal from the volume of interest,
wherein the signal is analyzed to determine a biochemical composition of a predetermined region of the predetermined segmented structure, wherein the predetermined region of the predetermined segmented structure corresponds to the volume of interest.

11. The method of claim 10, wherein the predetermined segmented structure is represented as a mesh, and the positioning includes positioning the volume of interest with respect to the predetermined segmented structure using mesh vertices as anchors.

12. The method of claim 10, further comprising:
generating a database of reference data by processing MRI image data corresponding to patients with known neurodegenerative disorders and patients with no neurodegenerative disorders and storing the biochemical compositions and a mapping between the biochemical compositions and the neurodegenerative disorders.

13. The method of claim 1, further comprising:
determining a biochemical biomarker by processing MRI image data corresponding to patients with a known neurodegenerative disorder, wherein the biochemical composition provides a signature biochemical biomarker of the known neurodegenerative disorder.

14. The method of claim 10, further comprising:
positioning the volume of interest with respect to the identified predetermined segmented structure of second MRI image data based on the one or more of the rules for positioning, wherein the volume of interest in the MRI image data and in the second MRI image data are positioned at the same location.

15. The method of claim 14, wherein the MRI image data and the second MRI image data correspond to a same patient; or
wherein the MRI image data and the second MRI image data correspond to different patients.

* * * * *